(12) United States Patent
Brutschin et al.

(10) Patent No.: US 7,818,990 B2
(45) Date of Patent: Oct. 26, 2010

(54) APPARATUS FOR DETERMINING AND/OR MONITORING A PROCESS VARIABLE OF A MEDIUM

(75) Inventors: Wolfgang Brutschin, Schopfheim (DE); Sascha D'Angelico, Rümmingen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 710 days.

(21) Appl. No.: 11/597,854

(22) PCT Filed: May 23, 2005

(86) PCT No.: PCT/EP2005/052355

§ 371 (c)(1),
(2), (4) Date: Aug. 28, 2007

(87) PCT Pub. No.: WO2005/119634

PCT Pub. Date: Dec. 15, 2005

(65) Prior Publication Data
US 2008/0134788 A1    Jun. 12, 2008

(30) Foreign Application Priority Data
Jun. 4, 2004    (DE) .................... 10 2004 027 397

(51) Int. Cl.
*G01F 25/00*    (2006.01)

(52) U.S. Cl. ........................................ 73/1.73; 73/1.83
(58) Field of Classification Search ................ 73/1.73, 73/1.83, 1.37; 324/543
See application file for complete search history.

(56) References Cited

U.S. PATENT DOCUMENTS

| 4,299,114 A | 11/1981 | Silvermetz |
| 5,777,550 A | 7/1998 | Maltby |

FOREIGN PATENT DOCUMENTS

| DE | 44 38 879 C1 | 2/1996 |
| DE | 198 35 370 A1 | 2/2000 |
| DE | 100 23 305 A1 | 11/2001 |
| EP | 0 810 423 A3 | 12/1997 |

*Primary Examiner*—John E Chapman
(74) *Attorney, Agent, or Firm*—Bacon & Thomas, PLLC

(57) ABSTRACT

An apparatus for determining and/or monitoring at least one process variable of a medium, and includes a sensor unit, a feedback electronics and a supplemental electronics. The sensor unit, feedback electronics and supplemental electronics form a first oscillatory circuit, which oscillates with at least one resonance frequency ($\omega_1$) and/or with a resonance frequency ($\omega_{res}$) within at least one resonance frequency range. The feedback electronics and the supplemental electronics form a second oscillatory circuit, which oscillates at a resonance frequency ($\omega_{cablebreak}$), which differs from the resonance frequency ($\omega_{res}$, $\omega_1$) of the first oscillatory circuit.

5 Claims, 3 Drawing Sheets

APPARATUS FOR DETERMINING AND/OR MONITORING A PROCESS VARIABLE OF A MEDIUM

Figure 1:
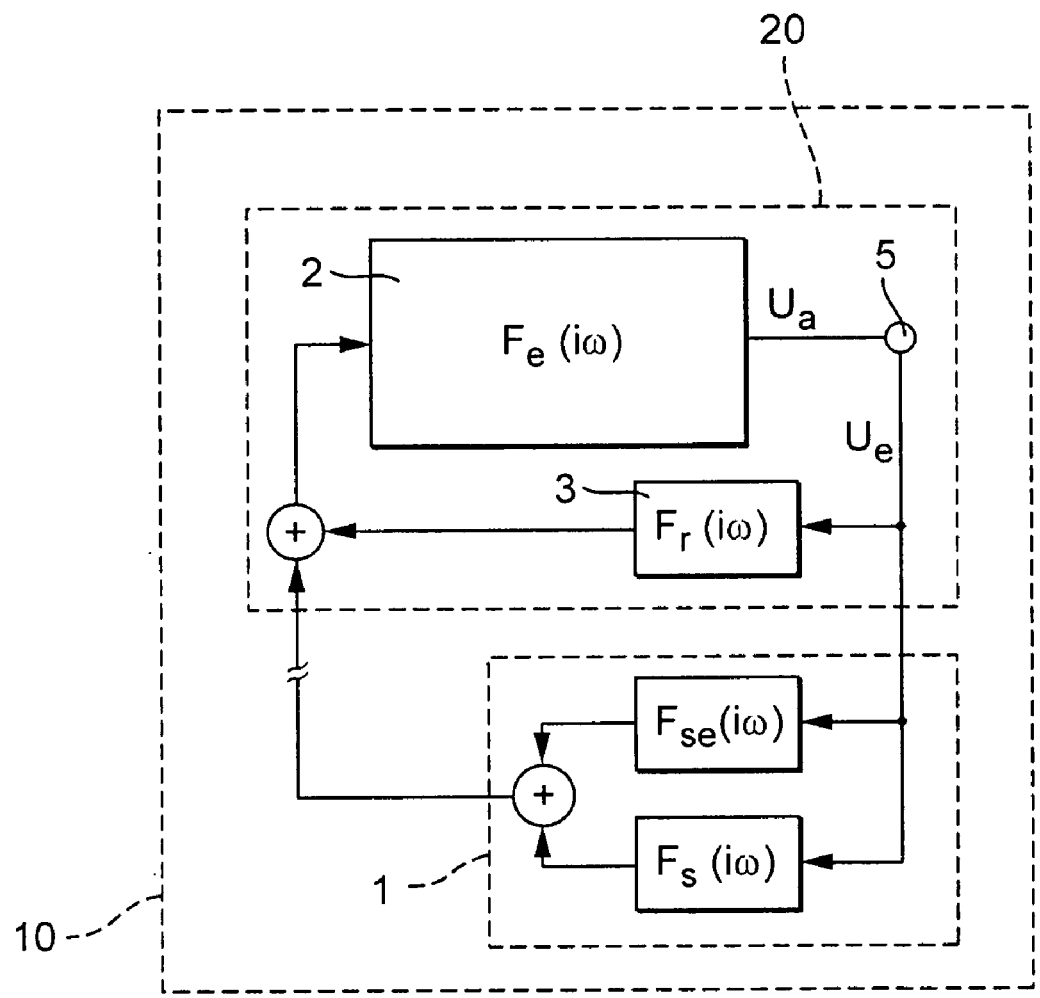

The invention relates to an apparatus for determining and/or monitoring at least one process variable of a medium. The process variable can be, for example, fill level, density, viscosity or flow of a medium. The medium can be a liquid or a bulk good.

The assignee manufactures and sells fill level measuring devices under the marks LIQUIPHANT and SOLIPHANT. Fill level is determined with a sensor unit having a mechanically oscillatable unit, e.g. an oscillatory fork, which is excited to oscillate via a piezo-transducer. The oscillations, for example their amplitude or frequency, depend on whether the oscillatable unit is freely oscillating, or whether it is covered by the medium. By this dependence, it is possible, for example, to determine fill level.

The piezo-transducer serves also for receiving the mechanical oscillations, which are thus converted into an electrical, alternating voltage. This alternating voltage, as signal of the oscillatable unit, is fed via appropriate connections to a feedback electronics, where the signal is amplified, simultaneously evaluated, and fed back again to the sensor unit. From the frequency, amplitude or phase of the signal coming from the sensor unit, then e.g. the fill level of the medium can be deduced. It is, however, also possible to determine the viscosity of the medium (see e.g. PCT-Application WO 02/31471 A2).

In vibronics, thus in processes using a mechanically oscillating unit, generally one distinguishes between the states "sensor covered" and "sensor free". If the connection between the sensor unit and the feedback electronics is interrupted, then such limit switches (the measuring devices serve for indicating whether a limit level has been reached) report, usually independently of whether they are in contact with medium or not, "covered", if at least one of the electrical connections between the feedback electronics and the sensor unit (usually the piezo-transducer) is interrupted. Such an interruption is e.g. possible, when the cable or connection locations become hard, because of the vibrations, and break. Such interruptions can also result from manufacturing errors or defects, with connections coming apart during operation of the measuring device, due to the vibrations. Such interruptions will be referenced for the following, generally and generically, as "cable break".

The patent DE 100 23 305 C2 indicates a method for recognizing such a cable break, wherein use is made of the fact that a piezo-transducer also functions as a capacitor, thus exhibiting a certain capacitance. On that basis, the capacitance, or a variable proportional thereto, is measured between the electrical leads to the piezo-transducer during excitation of the oscillations. If the capacitance falls below a predetermined, desired value, then a disturbance report is issued. This method has the disadvantage that an additional circuit is required, which produces an additional measured value, which must be evaluated. Besides frequency and/or amplitude of the oscillations, thus, also the capacitance is evaluated. This additional measured value contributes, beyond that, no additional information concerning the medium.

An object of the invention is to recognize a cable break between sensor unit and feedback electronics with a least possible effort and to characterize it distinguishably and certainly from the other states of the sensor.

The invention achieves the object by an apparatus for determining and/or monitoring at least one process variable of a medium, having a sensor unit, a feedback electronics, and a supplemental electronics, with the sensor unit, the feedback electronics and the supplemental electronics forming a first oscillatory circuit, with the first oscillatory circuit oscillating with at least a resonance frequency ($\omega_1$) and/or a resonance frequency ($\omega_{res}$) within at least a resonance frequency range, with the feedback electronics and the supplemental electronics forming a second oscillatory circuit, and with the second oscillatory circuit oscillating at a resonance frequency ($\omega_{cablebreak}$), which differs from the resonance frequency ($\omega_{res}$, $\omega_1$) of the first oscillatory circuit.

It is assumed that the frequencies $\omega_{res}$, $\omega_1$, $\omega_{cablebreak}$, or the frequency ranges connected therewith, differ sufficiently from one another. In any case, $\omega_{cablebreak}$ must differ from the frequencies, or frequency ranges, $\omega_{res}$ and $\omega_1$.

The invention relates, thus, to all measuring systems, which determine at least one process variable, e.g. fill level, wherein a sensor unit directly or indirectly comes in contact with the medium. In such case, it is possible, that, from the resonance frequency (mostly in the case of liquids) or from the oscillation amplitude (especially in the case of solids) at constant frequency, the process variable is deduced (see e.g. the above-mentioned application WO 02/31471 A2). Therefore, e.g. an above-described oscillatory fork can be involved; it can, however, also involve flow measurements according to the Coriolis principle.

An idea of the invention is that a supplemental electronics be introduced, which contributes thereto, that, in the case wherein, during normal operation of the apparatus, or measuring device, there are two different frequencies/frequency ranges, a third oscillation frequency is defined, from whose occurrence it can be deduced that a cable break has happened, that, thus, the sensor unit is no longer correctly connected with the remainder of the electronics of the measuring device.

In the case of an oscillatory fork, it is, for example, provided, that, in normal operation, the resonance frequency $\omega_{res}$ lies within a frequency range. This takes into consideration that, due to manufacturing deviations and tolerances, not all forks exhibit the same mechanical resonance frequency. Furthermore, this frequency range also includes the frequencies resulting from the free, and covered, states. Beyond such, different frequencies also arise from different densities and viscosities of the media.

Additionally, there is a so-called tear-off frequency $\omega_1$. Thus, it can happen, that, for example, by way of the medium (e.g. solids in a liquid) or because of mechanical damage, a mechanical oscillation of the sensor unit is no longer possible. For example, a fork tine can be broken off, or a solid particle is stuck between the fork tines. In this case, there remains only an electrical feedback; the oscillatable unit no longer influences the oscillatory circuit by means of its mechanical characteristics. In order to indicate this case, the system jumps to the mentioned, and defined, tear-off frequency $\omega_1$.

Consequently, a frequency band and an individual frequency are predetermined for the oscillatory fork. Or, in general, the first oscillatory circuit can oscillate at different frequencies, from which the process variable, or variables, is/are deduced, or which stand for other defined states, e.g. tear-off oscillation.

In the detection of solid particles, or bulk goods, usually only one frequency ($\omega_{res}$) occurs within a frequency band. In the case of these measuring devices, however, the frequency is not changed by contact with the medium.

The measuring device of the invention is, thus, to be understood as an oscillatory circuit composed essentially of three units: feedback electronics, sensor electronics, and supplemental electronics. The feedback electronics is also used for determining the process variable, in that e.g. via it, amplification, frequency or phase of the detected oscillations can be determined and evaluated. If all connections are functioning correctly, then, for example, the oscillations appear with the resonance frequency $\omega_{res}$ in the range of the predetermined frequency band, or the system oscillates with the tear-off frequency $\omega_1$ in the case of a mechanical impairment of the sensor unit. The frequencies are, in such case, dependent on the construction of the three units.

The units are, now, so connected together, that, in the case of a cable break between feedback electronics and sensor unit, the feedback electronics and the supplemental electronics form a second oscillatory circuit. This second oscillatory circuit oscillates, then, at a supplemental resonance frequency $\omega_{cablebreak}$, which, thus, uniquely indicates the cable break. By the invention, thus, in effect, a third resonance frequency (if, for the normal case, only one resonance frequency $\omega_{res}$ is provided, then it is a second resonance frequency that the supplemental electronics brings about) is provided, whose presence is an indicator for the cable break. There is, thus, a frequency (solids) or a frequency range (liquids), which results from normal operation. Additionally, there is a frequency for the state in which no mechanical oscillations are possible. And, by the invention, a supplemental frequency is provided, which indicates the case of cable break.

An embodiment of the apparatus of the invention includes, that the sensor unit and the supplemental electronics are connected in parallel and in series with the feedback electronics. By this embodiment, it is very easily implemented that first and second oscillatory circuits are provided, with the second oscillatory circuit resulting, when connection with the sensor unit is interrupted.

An advantageous embodiment of the apparatus of the invention provides, that the amplification of the first oscillatory circuit is, in the range of the resonance frequency, or resonance frequencies ($\omega_{res}$, $\omega_1$) of the first oscillatory circuit, greater than in the range of the resonance frequency ($\omega_{cablebreak}$) of the second oscillatory circuit. The advantage of this embodiment is that, in this way, it is prevented that the overall behavior of the apparatus, thus of the measuring device, is negatively influenced by the supplemental electronics. In principle, the first oscillatory circuit could oscillate at each of the three resonance frequencies, or frequencies and in the frequency range, as the case may be. In the concrete case, there remains the choice between one of the resonance frequencies for normal operation ($\omega_{res}$) and the frequency indicating cable break ($\omega_{cablebreak}$) and the choice between the tear-off frequency ($\omega_1$) and the cable break frequency ($\omega_{cablebreak}$). The choice between the frequency $\omega_{res}$ and the frequency $\omega_1$ is determined by the mechanical state of the sensor unit. Consequently, there remains of the three possibilities only the named pairings. Since the (circuit) amplification of the first oscillatory circuit (the amplification is composed of the amplifications of the three units) is, however, at the frequencies ($\omega_{res}$, $\omega_1$) actually of interest for the first oscillatory circuit, greater, preferably markedly, or much, greater, than for the resonance frequency ($\omega_{cablebreak}$) of the second oscillatory circuit, this resonance frequency ($\omega_{cablebreak}$) can scarcely appear in normal operation. Consequently, a condition, thus, for practical application is that this resonance frequency must, as much as possible, not appear during normal operation.

An embodiment alternative thereto, or in combination therewith, provides that the sum of the phases, which arise in the first oscillatory circuit, is essentially an integer multiple of $2\pi$, and that the sum of the phases, which arise in the second oscillatory circuit, is different from an integer multiple of $2\pi$, with the deviation from an integer multiple of $2\pi$ being of such a type, that the second oscillatory circuit is oscillatable. Thus, if the sensor unit is connected with the feedback electronics and the supplemental electronics, then, for the first oscillatory circuit, the sum of the individual phases is an integer multiple of 360°, or $2\pi$. In other words, at every point, at which one cuts the first oscillatory circuit, the incoming signal is in phase with the outgoing signal, i.e. the first oscillatory circuit can oscillate optimally. For the second oscillatory circuit composed of feedback electronics and supplemental electronics, however, the sum of the phases is preferably slightly different than an integer multiple of 360°, so that an oscillation of the first oscillatory circuit at the resonance frequency of the second oscillatory circuit is scarcely likely, yet an oscillation of the second oscillatory circuit is still possible. This is thus an alternative condition, in order to prevent a degrading of the measuring device by the supplemental electronics. Options include the adjusting of the amplification or of the phases or a suitable combination of both options.

An embodiment provides that, by a combination of the amplification of the first or the second oscillatory circuit and the sum of the phases of the first or second oscillatory circuit, it is assured, that an oscillation of the first oscillatory circuit at the resonance frequency ($\omega_{cablebreak}$) of the second oscillatory circuit is prevented. With this embodiment, thus, the phases and the amplifications, or gains, are combined with one another, so that an oscillation of the first oscillatory circuit at the resonance frequency ($\omega_{cablebreak}$) of the second oscillatory circuit is avoided. The two above embodiments are thus combined, in order to assure that the first oscillatory circuit does not oscillate at the resonance frequency of the second oscillatory circuit. In such case, various combinations of amplification or phase conditions are possible.

An embodiment includes, that the sensor unit has at least one mechanically oscillatable unit. The measuring device is, thus, for example, one including an oscillatory fork, or a so-called single-rod. In the case of such oscillatable units (oscillatory fork or single rod), usually also an exciter/receiver unit is provided, which produces the mechanical oscillations of the oscillatable unit and which received the oscillations. An embodiment thereof is a piezo-transducer, which is driven with an electrical alternating voltage, to convert such into a mechanical oscillation of the oscillatable unit, and which, in reverse, converts the mechanical oscillations into an alternating voltage. It can, however, also be an oscillating tube, or tubes, of a Coriolis flow measuring device. In the case of a single rod, or an oscillatory fork, the process variable is preferably the fill level of the medium; it can, however, also be the viscosity or density of the medium.

Figure 2A:
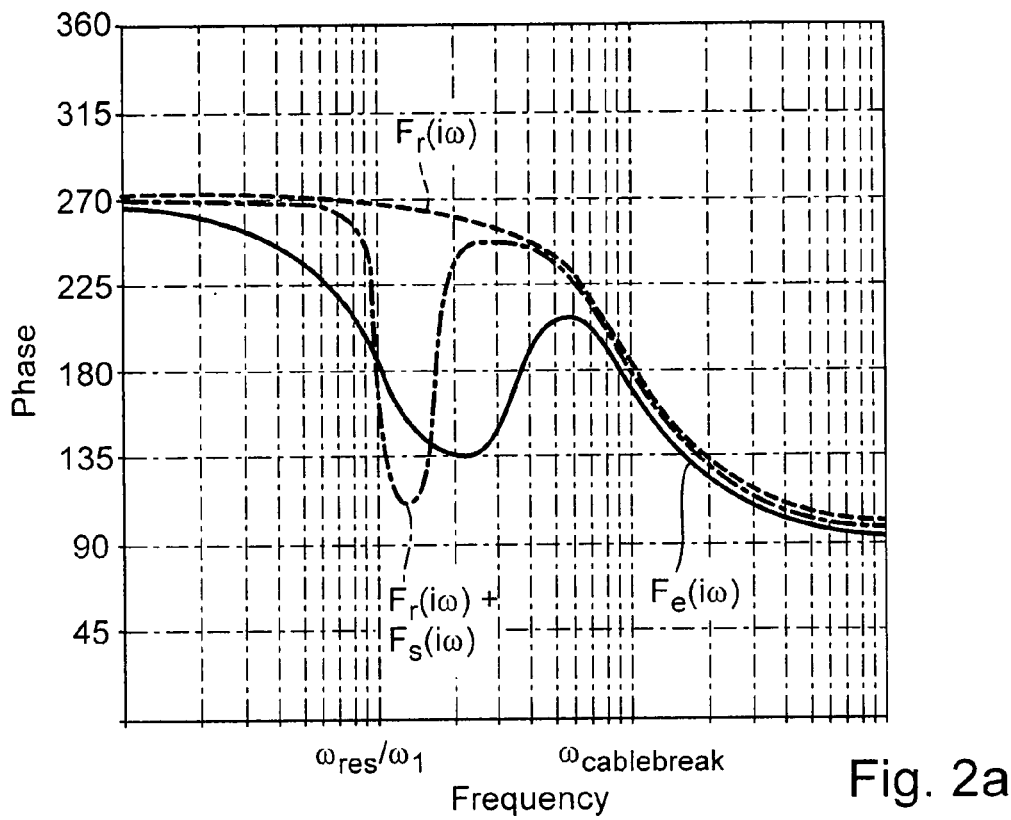
Figure 2B:
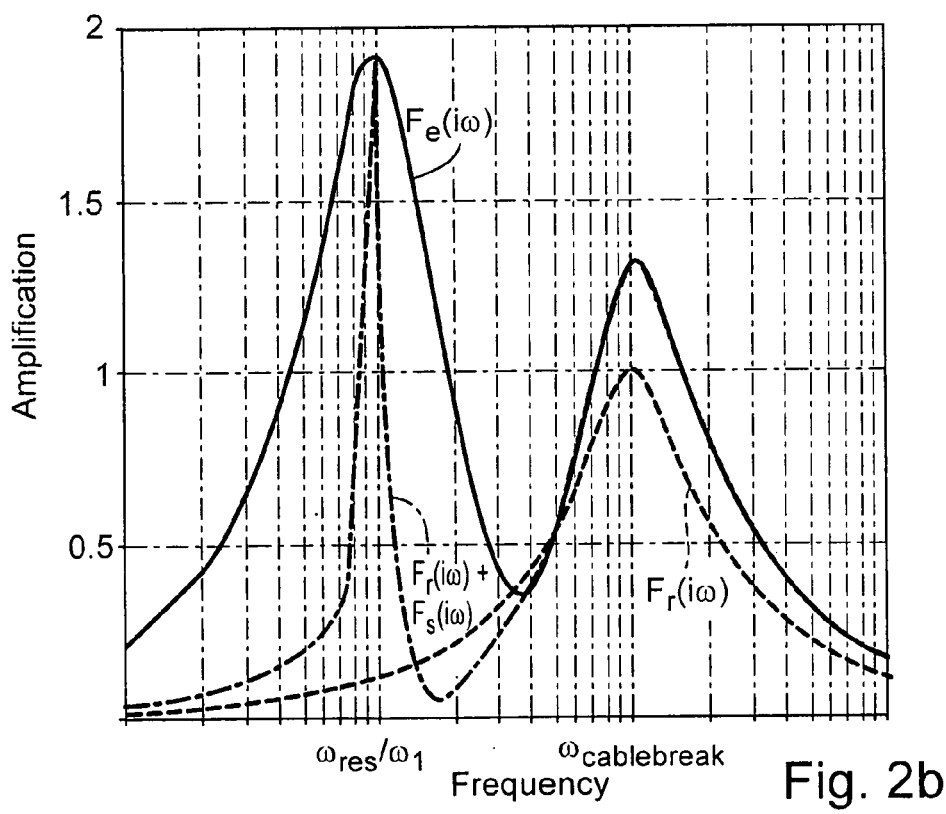
Figure 2C:
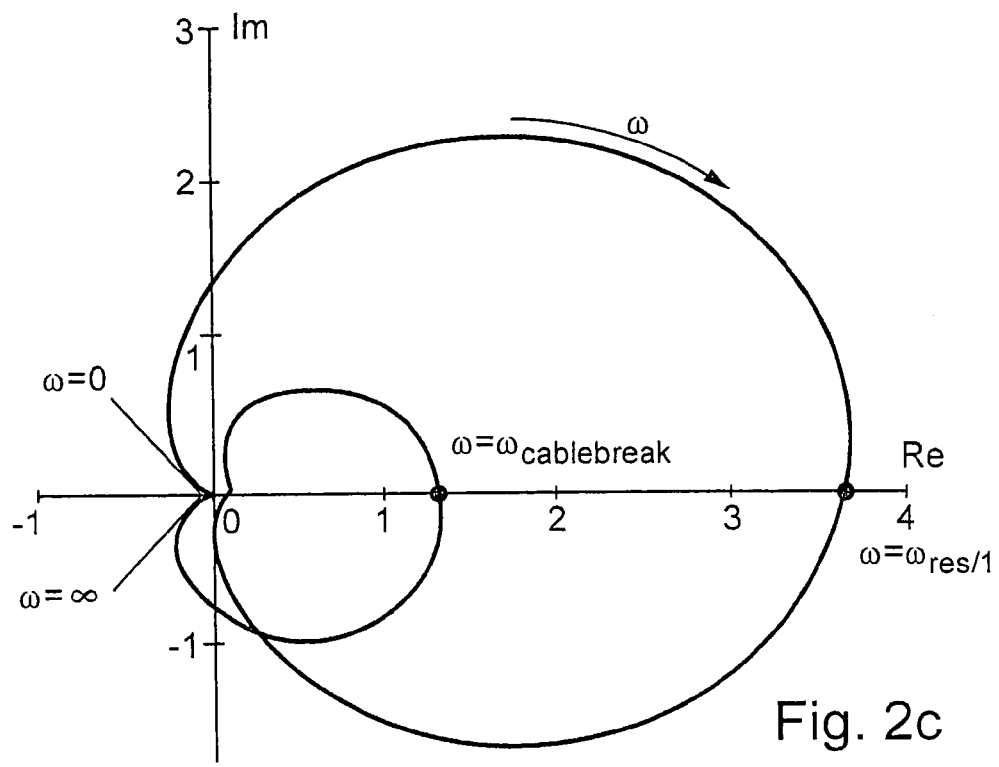
Figure 3:
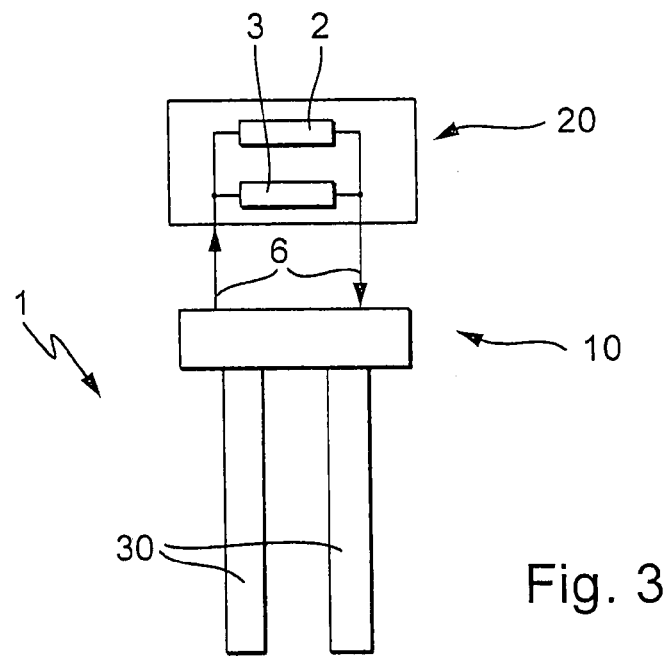

The invention will now be explained in greater detail on the basis of the appended drawings, the figures of which show as follows:

FIG. 1 a schematic, block diagram of the apparatus of the invention;

FIGS. 2a-c diagrams for describing the behavior of the apparatus of the invention; and FIG. 3 a schematic drawing of an oscillatory fork as an apparatus of the invention.

FIG. 1 is a schematic drawing of the apparatus of the invention. Shown are the sensor unit 1, the feedback electronics 2, and the added supplemental electronics 3 of the invention. These three units 1, 2, 3 form together the first oscillatory circuit 10, which oscillates, as a function of the process medium when it interact with the sensor unit 1, at one of the two resonance frequencies $\omega_{res}$ (this frequency is within a frequency band) or $\omega_1$ (in the case of tear-off oscillation, because mechanical oscillation of the sensor unit is no longer possible). Sensor unit 1 and the supplemental electronics 3 are connected in this embodiment in parallel and in series with the feedback electronics 2, so that the feedback electronics 2 and the supplemental electronics 3 form in the case of a cable break (indicated in the drawing by the two interruption hatchings) the second oscillatory 20 having the resonance frequency $\omega_{cablebreak}$.

For the following considerations, the parts labeled with $F(i\omega)$ are elements with complex transfer functions $F(i\omega)=U_{out}/U_{in}$. In particular, the following definitions hold:

Fe transfer function of the feedback, or amplifier, electronics 2;

Fr transfer function of the supplemental electronics 3 for generating the cablebreak state;

Fse transfer function of the purely electrical, sensor properties of the sensor unit 1 (sensor in the completely blocked state, wherein a mechanical oscillation is no longer possible); and Fs transfer function of the electric signals determined by the mechanical resonance oscillation of the oscillatable unit of the sensor unit (sensor is oscillating; it is in the free state, or in the covered state, or the mechanically oscillatable unit is partially covered, i.e. the sensor is in an intermediate state).

In order to describe the oscillatory circuits 10, 20, they are separated at the output 5. A possible signal saturation is, for the sake of simplicity, not considered (only the stationary case).

The oscillatory conditions of the various states then are as follows:

State 1—

The sensor can oscillate freely, or it can oscillate partially, or completely, covered, and no cable break is present:

$$\frac{U_o(i\omega)}{U_i(i\omega)} = [F_r(i\omega) + F_{se}(i\omega) + F_s(i\omega)] \times F_e(i\omega) = 1 + 0i \mid \omega = \omega_{res};$$

State 2—

The sensor is not oscillating, i.e. no mechanical oscillation is possible, and no cable break is present:

$$\frac{U_o(i\omega)}{U_i(i\omega)} = [F_r(i\omega) + F_{se}(i\omega) + 0] \times F_e(i\omega) = 1 + 0i \mid \omega = \omega_1;$$

and

State 3—

A cable break is present, with the sensor being oscillatable or not oscillatable:

$$\frac{U_o(i\omega)}{U_i(i\omega)} = F_r(i\omega) + F_e(i\omega) = 1 + 0i \mid \omega = \omega_{cablebreak}.$$

The resonant frequencies, in such case, are:

$\omega_{res}$—resonant frequency of the first oscillatory circuit 10 with the mechanical oscillation of the sensor, with the fork oscillating (either freely, or covered, or between these two extremes);

$\omega_1$—resonant frequency of the first oscillatory circuit 10 with fork completely covered and no longer able to oscillate (tear-off frequency), transfer function Fs of the oscillating sensor equal to 0; and $\omega_{cablebreak}$—resonant frequency of the second oscillatory circuit 20, which signals cable break, with the transfer functions Fs and Fse having fallen away, due to the cable break.

In order to distinguish states 2 and 3, $\omega_1 \neq \omega_{cablebreak}$ must hold. This is thus the first condition for implementing the apparatus of the invention. The same holds for the resonance frequency of the first oscillatory circuit 10 with the mechanical oscillation $\omega_{res}$ of the sensor.

Furthermore, it must be assured that the oscillation in the case of free sensor is scarcely influenced by the supplemental transfer element Fr, in that e.g. at given Fs, the transfer function Fr is so selected, that the following holds:

$$|F_r(i\omega_{cablebreak}) \times F_e(i\omega_{cablebreak})| < |[F_r(i\omega_{res}) + F_{se}(i\omega_{res}) + F_s(i\omega_{res})] \times F_e(i\omega_{res})|$$

This means that the circuit amplification of the first oscillatory circuit 10 in the region $\omega=\omega_{cablebreak}$ must be markedly smaller than in the region $\omega=\omega_{res}$ or $\omega=\omega_1$, as the case may be. This is a second condition for implementing the apparatus of the invention. This can be accomplished, as already indicated above, also via the phases.

In general, $\omega_{res}$ is a frequency interval determined by the mechanical, oscillatory characteristics of the sensor (manufacturing tolerances; density and damping characteristics of the medium in which the sensor is immersed; temperature; pressure).

Note: In a real electronics, due to complexity, the amplification is mostly not set equal to 1, but, instead, greater than 1. For a simplification of the formulas, the circuit amplification was set equal to 1. The above development does, however, describe the principles of the invention and the conditions for its implementation sufficiently.

In FIGS. 2a to 2c, the cable break detection by the apparatus of the invention is illustrated in more detail. For the sake of instruction, the situation is simplified in a manner such that the first oscillatory circuit oscillates only at a resonant frequency $\omega_{res/1}$, i.e. the above-described two states 1 and 2, which both relate to a "functioning" connection between the sensor unit and the feedback electronics, are brought together. In this way, thus, also the case is included, wherein, in normal operation, only one resonant frequency occurs, because e.g. the contact with the medium does not lead to a change of the oscillation frequency, but, instead, to a change of the oscillation amplitude (e.g. bulk goods, or solids, as opposed to liquids, whose different densities and viscosities result in the frequency range).

In FIGS. 2a and 2b, the curve Fe(i$\omega$) describes, in each case, the phase, or amplification curve, of the feedback electronics 2. The curve Fr(i$\omega$)+Fs(i$\omega$) describes the feedback of the first oscillatory circuit 10, and the curve Fr(i$\omega$) describes the supplemental electronics 3. The transfer function Fse(i$\omega$), thus the behavior in the case of covered oscillatory fork, is omitted, in order to simplify the presentation. The spectra in FIGS. 2a and 2b fulfill the oscillatory conditions for two different frequencies $\omega_{res/1}$ and $\omega_{cablebreak}$.

State ½:

The sensor unit is reporting free, or covered. No cable break is present. The curves Fe(i$\omega$) and Fr(i$\omega$)+Fs(i$\omega$)) hold:

$$[F_r(i\omega)+F_s(i\omega)] \times F_e(i\omega) \cong 1+0i$$

This equation is fulfilled for both frequencies $\omega_{res/1}$ and $\omega_{cablebreak}$. Since, however, for this state, also $|F_r(i\omega_{cablebreak}) \times F_e(i\omega_{cablebreak})| < |[F_r(i\omega_{res/1})+F_s(i\omega_{res/1})] \times F_e(i\omega_{res/1})|$ must be fulfilled, the first oscillatory circuit 10 oscillates at the frequency $\omega=\omega_{res/1}$. From the plot of the spectra, that can be reproduced. Thus, the normal behavior of the measuring apparatus is not influenced by the supplemental electronics 3 of the apparatus of the invention.

State 3:

The sensor unit is not connected; thus, a cable break is present. The curves $Fe(i\omega)$ und $Fr(i\omega))$ hold. In such case, for $\omega=\omega_{cablebreak}$, the following relationship is fulfilled:

$$F_r(i\omega) \times Fe(i\omega)=1+0i|\omega=\omega_{cablebreak}.$$

In the case of cable break, the second oscillatory circuit 20 thus oscillates at the cable-break frequency $\omega_{cablebreak}$, so that, from the appearance of this frequency, it can be deduced that such a cable break is present. And, especially by the amplification profile of the feedback electronics 2, it is assured that, in normal operation, thus with a connection present between the individual units, the first oscillatory circuit 10 oscillates assuredly at the resonant frequencies serving for determination of the process variable.

These states are also visible in the Nyquist plot in FIG. 2c. In the plot, the function $F(i\omega)=[F_r(i\omega)+F_s(i\omega)] \times F_e(i\omega)$ of the open oscillatory circuit is presented. With $\omega$ as parameter, one can travel along the function in the direction of the arrow from the origin ($\omega=0$), over the first oscillatory point ($\omega=\omega_{res/1}$) and the second ($\omega=\omega_{cablebreak}$), back into the origin ($\omega=\infty$). In the two oscillatory points, F is real, i.e. there is no phase shift between input and output, except for n*360°, where n is a natural number (n=1, 2, 3, ... ).

By the above conditions, the sensor unit 1, the feedback electronics 2 and the supplemental electronics 3 are sufficiently described, such that their implementation is within the skill of the art. In principle, it is only necessary to assure that the resonance frequency of the second oscillatory circuit 20 is different from the one or more resonance frequencies of the first oscillatory circuit 10, and that no negative influences are exerted by the supplemental electronics 3 on the oscillations of the first oscillatory circuit 10. This can be effected, for example, by assuring that the amplifying behavior of the first oscillatory circuit 10 in the range of the oscillations of the first oscillatory circuit 10 with the frequencies $\omega_{res}$ and $\omega_1$, as the case may be, is markedly greater than in the range of the oscillations of the second oscillatory circuit 20 with $\omega_{cablebreak}$.

FIG. 3 shows an oscillatory fork as the mechanically oscillatable unit 30 of an apparatus of the invention. Such a unit 30 is excited to oscillate by a piezo-transducer (not shown). If the apparatus is used for fill level determination, then fork 30 oscillates at two different frequencies $\omega_{res}$ (this is a frequency range, which is determined by the mechanical properties of the fork and by the properties of the medium, e.g. fill level, density or viscosity) or $\omega_1$ (the fork can not execute mechanical oscillations; tear-off frequency, when mechanical oscillations are absent). Problematic are the connections 6 between the sensor unit 1 and the feedback electronics 2, or the supplemental electronics 3. These connections are represented here by an exciter connection and a receiving connection; the situation may involve, however, a single, bi-directional connection. Such connections 6 can be cables, whose solder connections break, or which are attacked by an aggressive medium, which has penetrated into the apparatus. There are, thus, many ways by which a "cable break" can occur. This state, "cable break", is uniquely recognizable by the invention, in that, by the supplemental electronics 3, a second oscillatory circuit 20 is formed, which oscillates at a uniquely defined, resonant frequency $\omega_{cablebreak}$. And, by the structure of the first oscillatory circuit 10, or, particularly, by the design of the amplification characteristic of the sensor unit 1, the feedback electronics 2 and the supplemental electronics 3, it is assured that the first oscillatory circuit 10 does not oscillate at the cable-break frequency. Consequently, the second oscillatory circuit 20 only becomes active, when the connection 6 between supplemental electronics and the second oscillatory circuit 20 has been lost, thus when a cable break has occurred. Thus, the supplemental electronics 3 has the advantage that, by it, a well-defined frequency arises in the case of cable break, yet there is no negative influencing of normal operation.

LIST OF REFERENCE CHARACTERS 1 sensor unit
2 feedback electronics
3 supplemental electronics
5 point of separation
6 electrical connection
10 first oscillatory circuit
20 second oscillatory circuit
30 mechanically oscillatable unit

The invention claimed is:

1. An apparatus for determining and/or monitoring at least one process variable of a medium, comprising:
   a sensor unit;
   feedback electronics; and
   supplemental electronics, wherein:
   said sensor unit, said feedback electronics, and said supplemental electronics form a first oscillatory circuit;
   said first oscillatory circuit oscillates with at least a resonance frequency ($\omega_1$) and/or with a resonance frequency ($\omega_{res}$) within at least one resonance frequency range;
   in case of a cable break between said feedback electronics and said sensor unit, said feedback electronics and said supplemental electronics form a second oscillatory circuit; and
   in case of cable break, said second oscillatory circuit oscillates at a resonance frequency ($\omega_{cablebreak}$), which differs from the resonance frequency ($\omega_{res}$, $\omega_1$) of said first oscillatory circuit; and
   during normal operation the amplification of said first oscillatory circuit in the range of the resonance frequency or frequencies ($\omega_{res}$, $\omega_1$) of said first oscillatory circuit is greater than in the range of the resonance frequency ($\omega_{cablebreak}$) of said second oscillatory circuit.

2. The apparatus as claimed in claim 1, wherein:
   said sensor unit and said supplemental electronics are connected in parallel with each other and in series with said feedback electronics.

3. The apparatus as claimed in claim 1, wherein:
   during normal operation, the sum of the phases occurring in said first oscillatory circuit is essentially an integer multiple of $2\pi$; and
   the sum of the phases occurring in said second oscillatory circuit are different from an integer multiple of $2\pi$, wherein the deviation from an integer multiple of $2\pi$ is such that said second oscillatory circuit is capable of oscillation.

4. The apparatus as claimed in claim 1, wherein:
   during normal operation, by a combination of the amplification of said first or said second oscillatory circuit and of the sum of the phases of said first or said second oscillatory circuit, it is assured that an oscillation of said first oscillatory circuit at the resonance frequency ($\omega_{cablebreak}$) of said second oscillatory circuit is prevented.

5. The apparatus as claimed in claim 1, wherein:
   said sensor unit has at least one mechanically oscillatable unit.

* * * * *